(12) United States Patent
Papendick et al.

(10) Patent No.: US 7,195,617 B2
(45) Date of Patent: Mar. 27, 2007

(54) DEVICE FOR COLLECTING SURGICAL MATERIAL

(75) Inventors: Lew Papendick, Rapid City, SD (US); Thomas Blue, Rapid City, SD (US)

(73) Assignee: Six-O, Ltd., Rapid City, SD (US)

(*) Notice: Subject to any disclaimer, the term of this patent is extended or adjusted under 35 U.S.C. 154(b) by 0 days.

(21) Appl. No.: 10/792,448

(22) Filed: Mar. 3, 2004

(65) Prior Publication Data

US 2005/0197638 A1    Sep. 8, 2005

(51) Int. Cl.
*A61M 1/00* (2006.01)

(52) U.S. Cl. .................. 604/317; 604/327; 604/356; 4/144.1; 4/144.3

(58) Field of Classification Search ........ 604/317–324, 604/327, 356; 222/511, 516–517; 220/411, 220/416, 418; 4/144.1, 144.3
See application file for complete search history.

(56) References Cited

U.S. PATENT DOCUMENTS

| | | | | |
|---|---|---|---|---|
| 3,575,225 A * | 4/1971 | Muheim | ................... | 383/206 |
| 3,841,333 A | 10/1974 | Zalucki | ................... | 604/330 |
| 4,671,708 A | 6/1987 | Hurd | ................... | 406/108 |
| 4,798,292 A | 1/1989 | Hauze | ................... | 206/439 |
| 4,967,763 A | 11/1990 | Nugent et al. | ................... | 128/763 |
| 5,269,785 A | 12/1993 | Bonutti | ................... | 606/80 |
| 5,320,115 A | 6/1994 | Kenna | ................... | 128/898 |
| 5,366,457 A | 11/1994 | McGuire et al. | ................... | 606/86 |
| 5,570,706 A | 11/1996 | Howell | ................... | 128/898 |
| 5,662,710 A | 9/1997 | Bonutti | ................... | 623/11 |
| 5,683,406 A | 11/1997 | Altobelli et al. | ................... | 606/170 |
| 5,792,126 A | 8/1998 | Tribastone et al. | ................... | 604/319 |
| 5,865,834 A | 2/1999 | McGuire | ................... | 606/80 |
| 5,913,859 A | 6/1999 | Shapira | ................... | 606/80 |
| 5,920,916 A | 7/1999 | Norton | ................... | 4/144.3 |
| 5,951,561 A | 9/1999 | Pepper et al. | ................... | 606/80 |
| 5,954,961 A | 9/1999 | Carchidi | ................... | 210/452 |
| 6,022,354 A | 2/2000 | Mercuri et al. | ................... | 606/80 |
| 6,045,554 A | 4/2000 | Grooms et al. | ................... | 606/73 |
| 6,325,804 B1 | 12/2001 | Wenstrom, Jr. et al. | ................... | 606/72 |
| 6,352,538 B2 | 3/2002 | McGuire et al. | ................... | 606/86 |
| 6,379,384 B1 | 4/2002 | McKernan et al. | ................... | 623/13.12 |
| 6,395,011 B1 | 5/2002 | Johanson et al. | ................... | 606/179 |
| 6,447,516 B1 | 9/2002 | Bonutti | ................... | 606/72 |
| 6,494,869 B1 | 12/2002 | Hand et al. | ................... | 604/319 |
| 6,723,078 B1 | 4/2004 | Pennington et al. | ................... | 604/327 |
| 6,872,184 B2 | 3/2005 | Brannon | ................... | 600/562 |

* cited by examiner

*Primary Examiner*—Tatyana Zalukaeva
*Assistant Examiner*—Melanie J Hand
(74) *Attorney, Agent, or Firm*—Westman, Champlin & Kelly, P.A.

(57) ABSTRACT

A collection device for collecting material during a surgical procedure includes a collection chamber defined by an encompassing wall and having an opening sufficient for permitting collection of the material during the surgical procedure. A wicking material is positioned outside the collection chamber and is in fluid association therewith sufficient to wick fluid from within the collection chamber. The device also includes a scoop wall extending from the collection chamber and having a distal end portion for positioning proximate a source of the material and for guiding the material to the collection chamber wherein the scoop wall includes curved sidewall portions that are separated from the encompassing wall such that the scoop wall is bendable with respect to the chamber.

21 Claims, 7 Drawing Sheets

DEVICE FOR COLLECTING SURGICAL MATERIAL

BACKGROUND OF THE INVENTION

The present invention relates to the field of surgery, and particularly, to the field of knee surgery. More specifically, the present invention relates to a device for the harvesting of bone reamings produced during anterior cruciate ligament reconstruction surgery.

One of the more commonly performed procedures in knee surgery is reconstruction of the anterior cruciate ligament. These reconstructions are almost always done arthroscopically. One of the problems faced in anterior cruciate ligament knee surgery is that defects are created in the bone during surgery. One such defect is called the patellar defect.

For several reasons, bone reamings resulting from the surgery provide the most desirable material for treating a bone defect. The reamings provide greater surface area of bone, which promotes healing. The reamings are more pliable than other bone material and therefore, mold well to the shape of the patellar defect. Other types of grafting material such as bone core and curetting tibial bone have time, difficulty, and cost disadvantages. It takes more time for a surgeon to use a bone core because it is rigid and has to be sized, cut and formed to fit the defect. It is also more difficult for a surgeon to work with and is more costly because of the additional operating room and staff time needed. Due to a bone core's rigidity, even after taking the time to size, cut and form the bone, it does not fit the defect as well as reamings. In addition to the same time, difficulty, and cost disadvantages of using a bone core, curetting tibial bone from the tibial defect at the harvest site creates further morbidity to the tibia. Additionally, autogenous grafting material provides the most optimal healing and effective recovery for the patient.

It has been known to use a stiff metal medicine cup to attempt to collect bone chips from reamings for use as grafting material in anterior cruciate ligament reconstruction surgery.

BRIEF SUMMARY OF THE INVENTION

The present invention includes a collection device for collecting material during a surgical procedure. The device includes a collection chamber defined by an encompassing wall and having an opening sufficient for permitting collection of the material during the surgical procedure. A wicking material is positioned outside the collection chamber and is in fluid association with an interior of the chamber sufficiently to wick fluid from within the collection chamber. The device also includes a scoop wall extending from the encompassing wall and having a distal end portion for being positioned proximate a source of the material and for guiding the material to the collection chamber wherein the scoop wall includes curved sidewall portions that are separated from the encompassing wall such that the scoop wall is bendable with respect to the chamber.

DETAILED DESCRIPTION

The present invention allows for collection of surgical materials, such as bone reamings during anterior cruciate ligament (ACL) knee surgery. The collected reamings may later be used as autogenous graft material.

Figure 1:
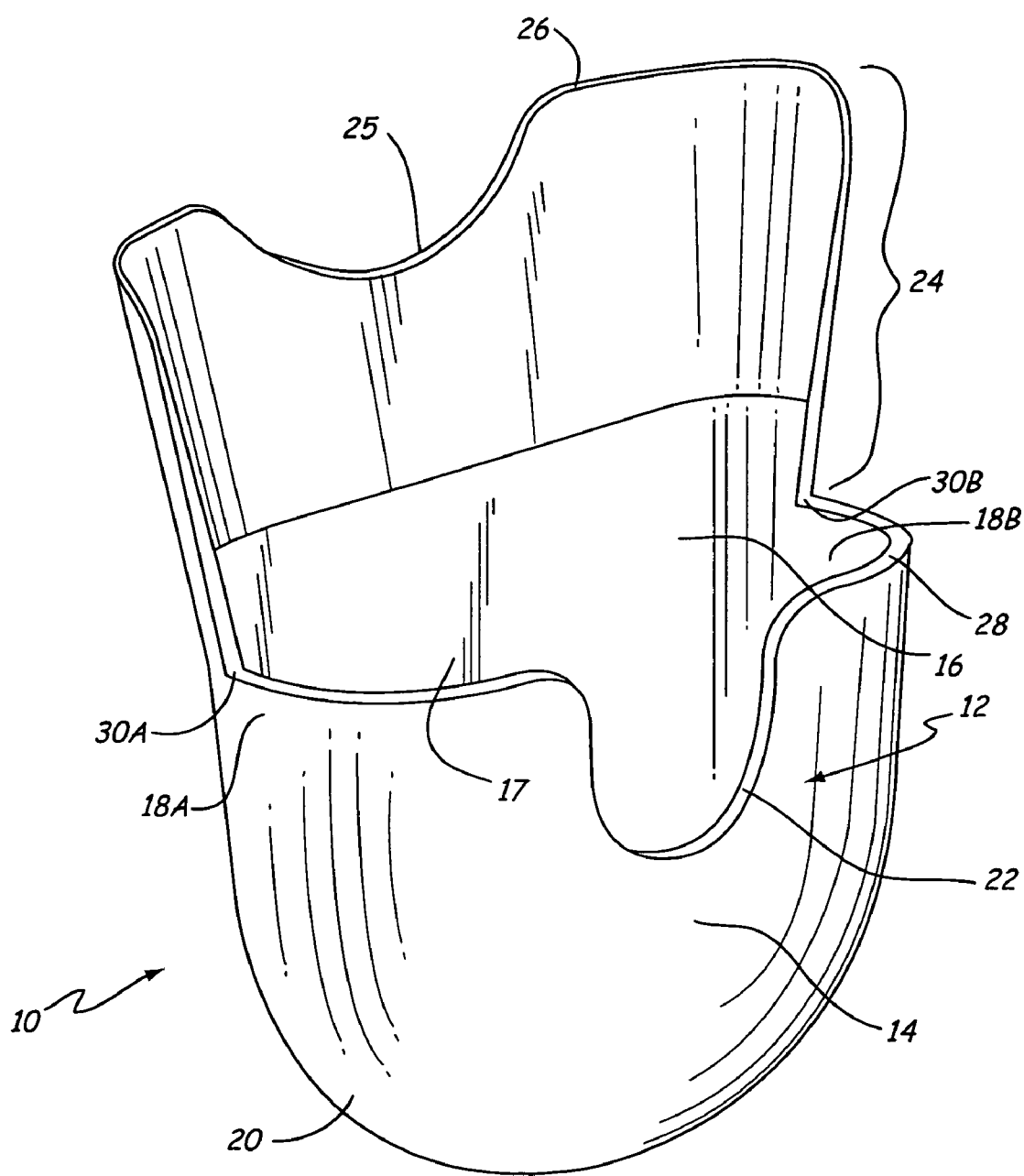
FIG. 1 is a perspective view showing the front and side of the present invention.

Bone reamings (chips) created during surgery are generally not utilized or are underutilized as autogenous bone graft material because there are no current generally accepted collection methods that allow for efficient and effective collection and separation of the reamings. A collection device of the present invention generally indicated at 10 in FIG. 1, allows a surgeon to readily gather, separate, and apply bone reamings as graft material during surgery.

The collection device 10 is comprised of a collection chamber 12 and a scoop wall 24. Throughout the drawings, like reference characters will be used to indicate like elements. The collection chamber 12 is formed from a front face 14 and a back face 16 defining an opening 17. The front face 14 and the back face 16 are connected at sides 18A, 18B, and bottom 20. As illustrated in the exemplary embodiment, the connection between the front face 14 and the back face 16 is seamless and forms an encompassing wall that defines the collection chamber 12. The upper center of the front face 14 has a cutout 22 that facilitates the surgeon's use of a reamer. The cutout on the front of the device allows it to be positioned on the patient's leg below the site where the reamer enters the body to create the tibial tunnel while not interfering with the reamer positioning or the proper angle the surgeon needs for correctly creating the tibial bone tunnel. In the exemplary embodiment, the cutout 22 is approximately 0.830 inch wide and 0.788 inch in length, which is about twice the size of a typical reamer used in ACL reconstruction surgery. The cutout being larger than the diameter of the reamer permits angular positioning and repositioning if needed of the reamer in the cutout.

The back face 16 of the collection chamber 12 is extended and forms the scoop wall 24. The scoop wall 24 serves as a collection surface for the collection chamber 12, in which the scoop wall 24 functions as a slide, scoop or funnel. The dimensions of the scoop wall 24 can vary. Additionally, in the exemplary embodiment, the back face 16 is integral with the scoop wall 24 as one continuous piece. Variations of the extended rear surface of the collection chamber 12 can include the back face 16 and the scoop wall 24 as two separate pieces which are then connected or attached to form the extended back surface.

The scoop wall 24 also includes a depression 25 disposed centrally at a top edge 26 which allows for better positioning of the reamer and the scoop wall 24 against the leg. The scoop wall 24 includes a central portion and sidewall portions 30A and 30B. The sidewall portions 30A and 30B extend outwardly from the central portion and curve forwardly to form a channel to guide bone reamings to the collection chamber 12. In this exemplary embodiment, the scoop wall 24 is approximately 1.394 inches in length (when measured from the top edge 26 of the scoop wall 24 to the collection chamber top edge 28) not taking into account the depression which is approximately 1.0 cm and approximately 2.572 inches in width.

The scoop wall 24 is tapered such that a portion closer to the collection chamber 12 has the same thickness as the collection chamber 12, which is approximately 0.062 inch in the exemplary embodiment. The thickness of scoop wall 24 begins to taper off approximately one third of the way distal from the defined back face 16 of the collection chamber 12 to a final thickness of approximately 0.025 inch at a top edge 26. The tapered surface of the scoop wall 24 allows for the top portion of scoop wall 24 to be more flexible to conform to the patient's leg below the operative site.

Figure 5:
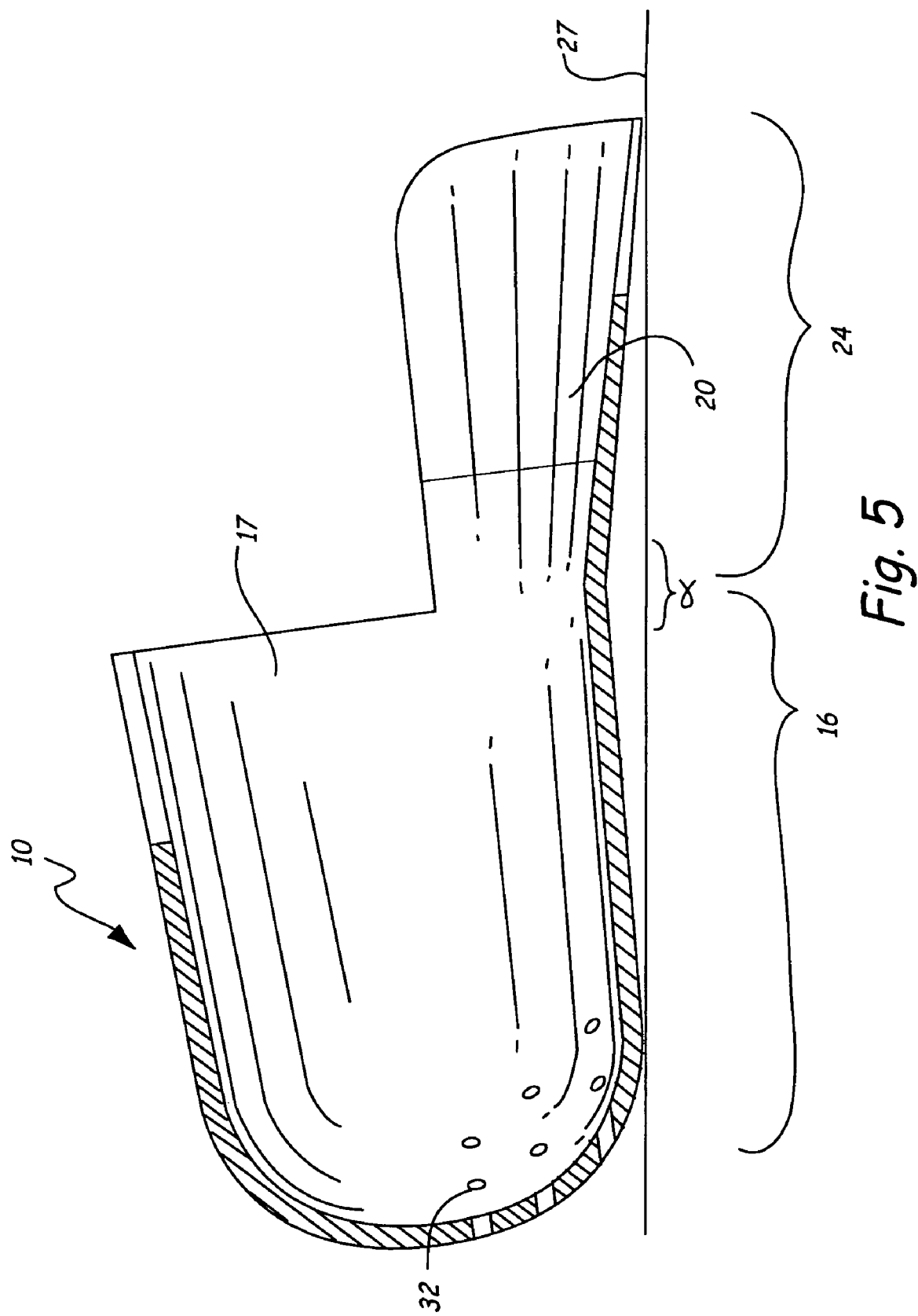
FIG. 5 is a sectional view of the device on a surface in a resting position.
Figure 6:
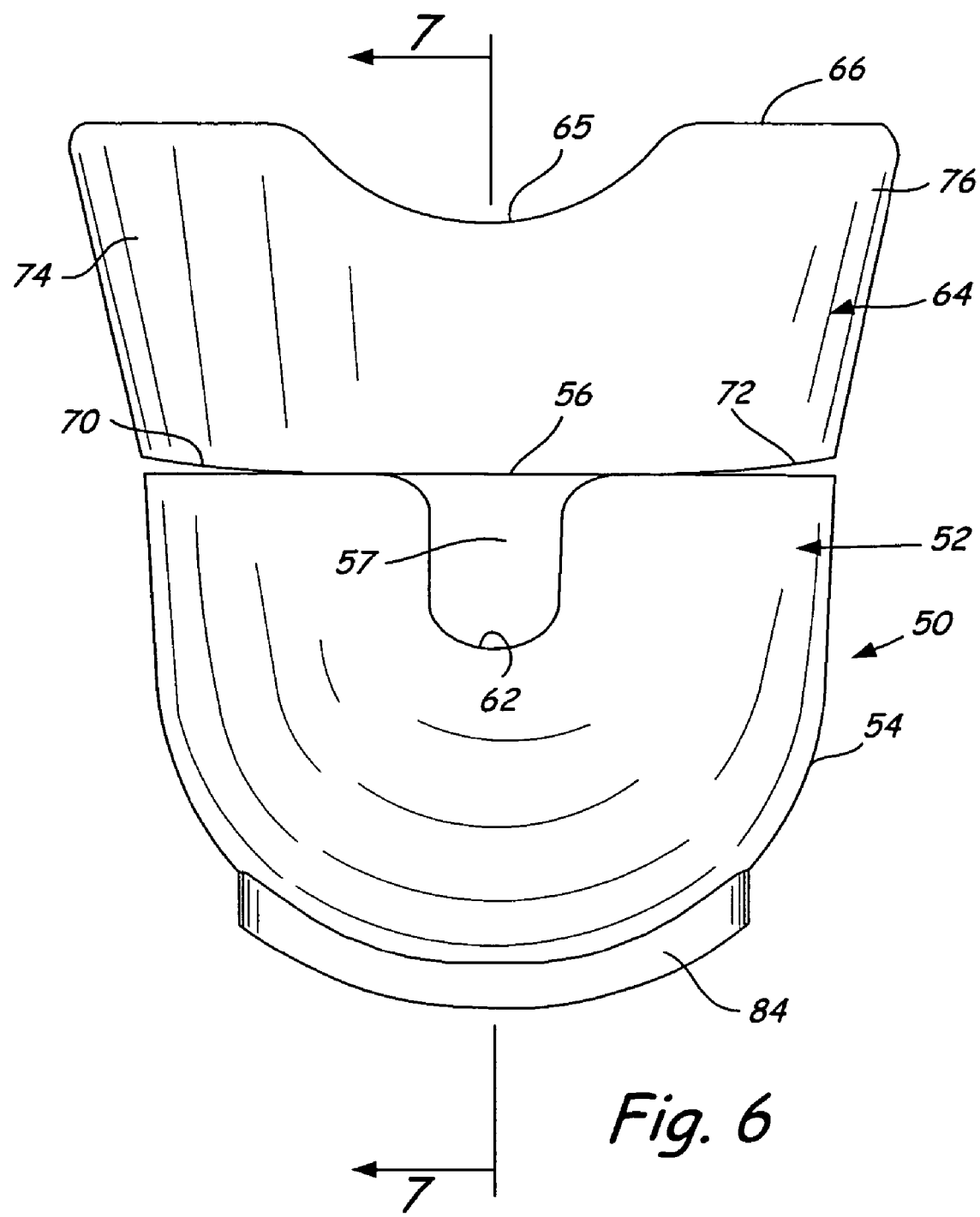
FIG. 6 is a front elevational view of an alternative embodiment of the present invention.

The scoop wall 24 forms an obtuse angle a with the back face 16 of the collection chamber 12 so that when the device 10 is placed on a surface 27 such as a table, the bone chips are retained within the chamber 12 as is seen in FIG. 5. When placed on a surface, the collection chamber 12 is tilted upwardly, to retain the bone chips.

On the lower portion of the back face 16 of the collection chamber 12 are openings 32 through which fluid drains from the collection chamber 12. In the exemplary embodiment, there are eighteen openings 32 that are approximately 0.12 inches each in diameter. The openings 32 are set apart approximately 0.25 inches horizontally and approximately 0.187 inches vertically. The openings 32 are positioned in three rows with five openings 32 in the row closest to the back face 16, six openings 32 in the middle row and seven openings 32 in the row closest to the front face 14. However, the openings 32 can be located anywhere within the collection chamber and in any formation so long as fluid continues to drain from the chamber when the device is held or is placed on a surface. When the chamber is filled with bone chips, the bone chips may stop fluid from flowing from the chamber through the openings 32. The device may then be pressed against or placed on a sponge to wick away further liquid from the chamber before the bone chips are used as explained subsequently below.

Figure 2:
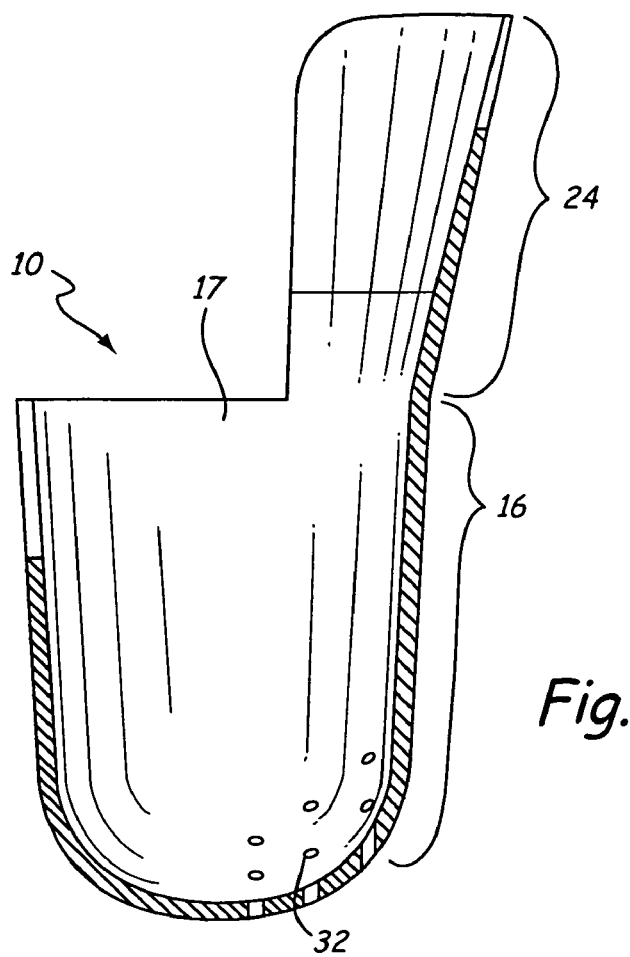
FIG. 2 is a sectional view taken along the line 2—2 in FIG. 4.
Figure 4:
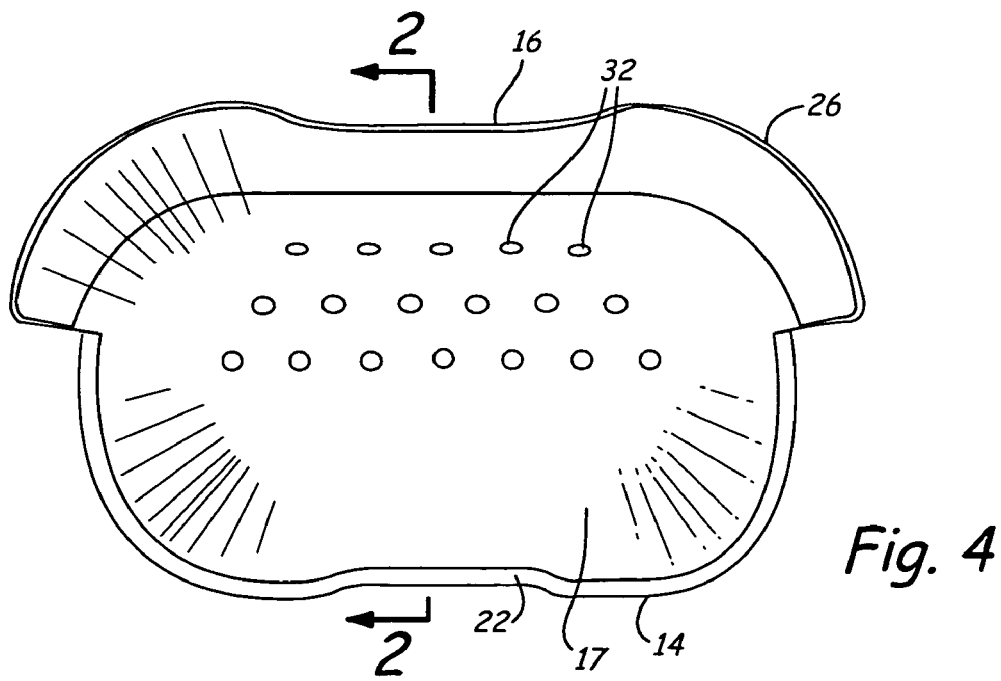
FIG. 4 is a top view of the present invention.

When used during surgical procedures, the collection device 10 is placed below a reamer 44 with the scoop wall 24 pressed against the leg just below the operative site. While the reamer 44 is being used to create a tunnel in the bone, the lower portion of the reamer 44 can be maneuvered because of the space created by the cutout 22 in the upper front face 14 of the collection chamber 12. Bone reaming expelled from the tunnel slide down the scoop wall 24 and fall into the collection chamber 12. The bone reamings settle to the bottom of the collection chamber. Some saline or other fluids are then slowly poured from the device over 18A or 18B and the remaining fluids are allowed to drain from the collection device 10 through openings 32 in collection chamber 12. As illustrated in FIGS. 2 and 4, the openings 32 are of a size to provide efficient draining of fluids while retaining the majority of the reamings. In addition, the collection device is of a sufficient width that when positioned below the operative site a major portion of the bone reamings that are generated are deposited within the collection device. Although a collection device having a substantially cylindrical configuration will collect bone reamings, a device having a substantially oval or rectangular configuration and whose backwall can be placed to conform to the surface next to the operative site and which will conform to a surface of the operative site collects a major portion of the bone reamings being generated.

To understand the context in which the present invention is used, the following is a description of the surgical procedure. The order of some of these "steps", especially 5 and 6, can be changed and often are depending on when the bone-tendon-bone (B-T-B) graft is ready. To begin the procedure, a patient is placed in a supine position with a tourniquet on the operative proximal thigh. The thigh is placed in a leg holder with the foot of the bed down at 90 degrees, allowing the knee to bend 90 degrees. The leg is then prepped and draped in the routine sterile fashion. A superolateral portal is placed just proximal and lateral to the patella, and the inflow cannula is placed in the portal. Saline is pumped into the knee with the inflow pump. The standard anterolateral and anteromedial portals are established. Once the portals are established, the procedure can be divided into six basic steps: 1. Debride the torn ACL and perform an intercondylar notchplasty, 2. Harvest B-T-B Graft from patella/tibia, 3. Ream tibial tunnel and collect reamings, 4. Ream femoral tunnel, 5. Pass and secure B-T-B ACL graft (that surgeon harvested from the patella/patella tendon/tibia), and 6. Place reamings in patellar defect and close peritenon. The order of the steps are interchangeable.

First, torn fragments of the ACL are debrided with a standard arthroscopic shaver through the anteromedial portal. The notchplasty is then performed, taking bone from the lateral and superior edge of the intercondylar notch of the femur. An arthroscopic burr is used to abrade bone and soft tissue in the intercondylar femoral notch until the femoral attachment of the ACL is visualized. The burr is then used to make a small divot approximately 2–3 mm from the over-the-top position at either the 11 o'clock (right knee) or 1 o'clock (left knee) position in the intercondylar notch of the femur.

Second, a skin incision is made adjacent to the patellar tendon. It is carried through the subcutaneous tissue to the peritenon. Retraction of skin and subcutaneous tissue is accomplished to visualize the entire patellar tendon from the tibial tubercle to the patella. The peritenon is then split midline and stripped from the patella and patellar tendon to give full visualization of the patellar tendon in its medial to lateral width. The central one-third of the patellar tendon is then harvested.

Using a powered saw blade, the patella is cut at approximately a 60 degree angle both on the medial and lateral sides. A slightly angled cut is also made on the cephalad surface. An osteotome is then used to wedge the pie-shaped piece of bone out of the patella. On the distal end similar saw cuts are made in the tibia and the autogenous graft is then lifted. At this point, the surgeon has obtained a fragment of the patellar bone, a piece of patellar tendon and a fragment of the tibial tubercle. The wound is then thoroughly irrigated.

Third, with electrocautery, an incision is made on the tibia just proximal to the attachment of the pes anserine tendons, midway between the anterior and posterior edge on the medial side of the tibia. The area is stripped of its periosteum to give access for the tibial guide used to produce the tibial tunnel.

With the arthroscope in the anterolateral portal, the tibial guide is then placed in the anteromedial portal. A guidepin is drilled from the external surface of the tibia to the above-mentioned site intra-articularly. Generally, the tibial guide is placed so that the guidepin of the tibial guide will exit intra-articularly in the footprint of the ACL at approximately the junction of the attachment of the posterior edge of the anterior horn of the lateral meniscus.

Figure 3:
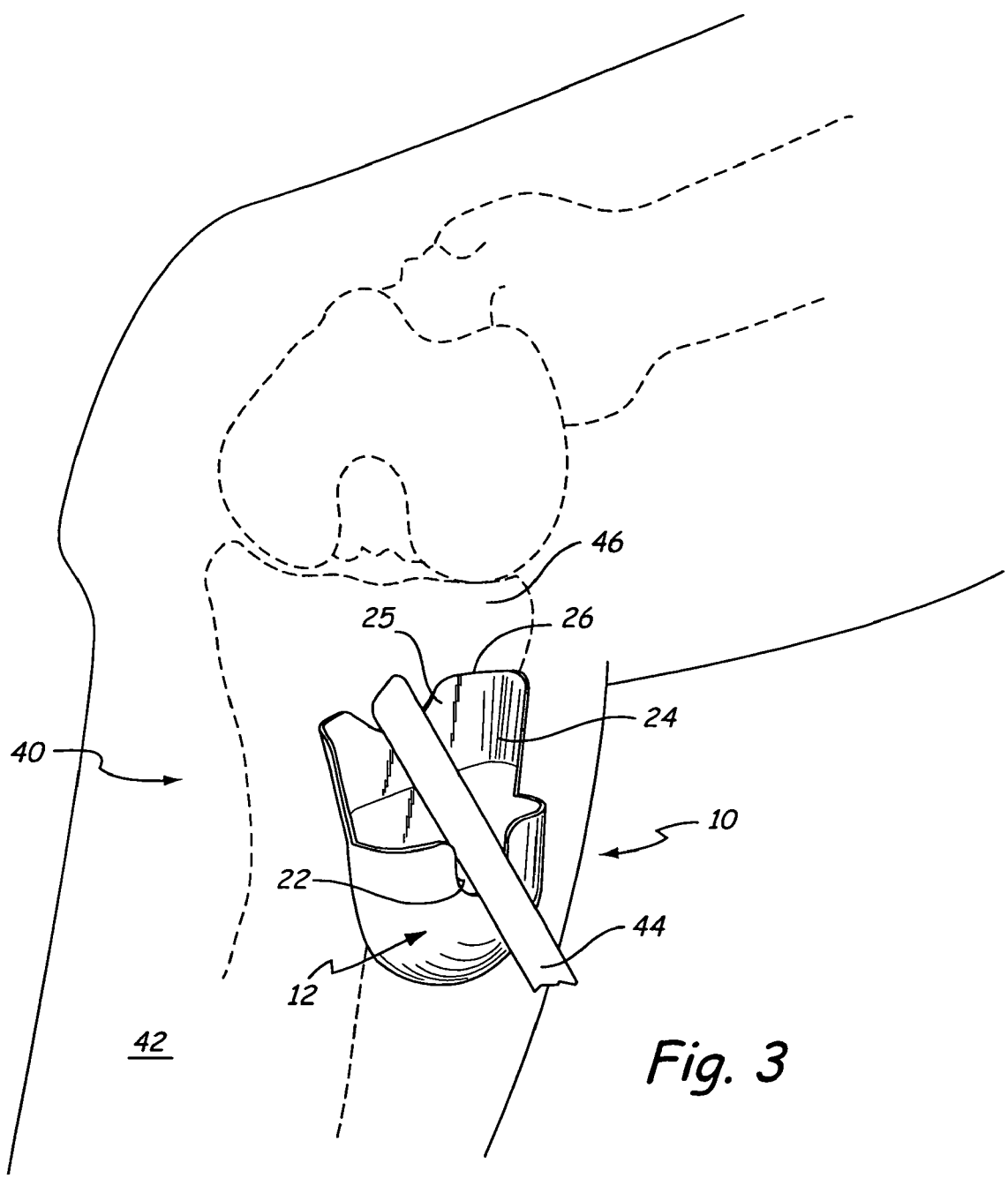
FIG. 3 is a perspective view illustrating the present invention in use.

As illustrated in FIG. 3, the bone collection device 10 is manually held by the surgeon (not shown) and/or an operating room assistant (not shown) against the leg 40 on the external surface 42 so that the collecting surface, scoop wall 24, is held firmly just below the reamer 44. The tibia 46 is illustrated in broken lines. The scoop wall 24 is flexible such that it conforms to the surface 42 of the leg 40. However, alternatively, if the device of the present invention did not include the scoop wall 24, but instead just the chamber, the chamber wall could also be sufficiently flexible to conform to the surface of the leg. As the surgeon (not shown) creates the tibial tunnel with a standard rigid reamer, bone reamings are collected and pulled toward the external surface and into the device. Once the reamer enters the "joint", the saline or other fluid earlier pressurized by an inflow pump to create extension within the knee joint releases suddenly through the tibial tunnel. Saline and reamings flush rapidly from the tunnel, down the scoop wall 24 and into the collection chamber 12. As the saline immediately begins to drain out of the collection chamber 12 including via the openings 32 along the bottom 20 of the collection chamber 12, the majority of the reamings are retained. Since they are denser than the fluids, the reamings settle to the bottom of the collection chamber but do not flow through the openings 32.

The majority of the fluid in the collection chamber 12 is then slowly poured over either side 18A or 18B with care taken not to pour out the bone graft reamings. The collection device 10 is set down with back face 16 facing downwardly and placed on or pressed against a sponge (not shown) to permit remaining fluids to continue draining and wicking through the openings 32. As illustrated in FIG. 5, the reamings are maintained in the collection chamber 12, because of the obtuse angle between the scoop wall and the back face 16 of the chamber 12. This angled feature also helps the collection device 10 to continue to drain fluids when set down. Once the fluids have drained, the reamings can be used as graft material.

Fourth, the tibial guidepin is then placed through the tibial tunnel, up through the intraarticular area, through the femoral notch, and into the burred hole on the posterior aspect of the intercondylar notch at the femoral attachment of the ACL. The tibial guidepin is then pounded in a couple of millimeters. An acorn reamer is then brought in over the guidepin and the femoral tunnel is reamed up to the inner side of cortical bone.

As the saline inflow is pumping and a tunnel plug placed in the tibial tunnel to maintain fluid within the knee joint, an arthroscopic debrider blade is used to suction out and debride out any excess bone fragments from the femoral tunnel and knee joint. Other soft tissue debris is also debrided at this time.

There are many known options for the femoral fixation and it is intended that all are included within the present invention. The method described herein is the endo button fixation. For this method, a guidepin is brought through the tibial tunnel into the femoral tunnel. The guidepin is then drilled through the outer cortex of the femur. An endo button reamer is then brought over the guidepin and a hole is reamed in the femoral cortex. A depth gauge is then utilized to measure the femoral tunnel length. This length is utilized to secure the endo button to the ACL graft.

Fifth, a passing pin is manually brought from the tibial side through the tibial tunnel, the intraarticular area and the femoral tunnel and carried through the skin over the femur. The B-T-B ACL autograft, harvested earlier, is then brought through the tibial and then into the femoral tunnels by placing sutures, which are in the endobutton, into the passing pin. The passing pin with sutures and graft is then pulled through both tunnels, the endo button hole, and quadriceps muscle and skin. Using the sutures the graft is pulled up into the joint, into the femoral tunnel with the endo button. It is advanced until the endobutton is pulled through the femoral cortex, thus the graft is in the anatomic position.

The endo button is flipped so it locks on the outer cortex of the femur. The graft is then pulled distally giving femoral fixation. When this is completed approximately 28 mm of patellar tendon from the graft are centered within the articular surface and the bone portions of the graft are within the bone tunnels of the femur and tibia respectively. The endo button is locked on the femoral side and distal traction can be placed on the graft with the sutures in the tibial side of the graft. The knee is brought into extension to ensure that there is no impingement on the graft within the femoral notch. At this point, a hole is drilled in the tibia just distal to the tibial tunnel. A screw with a washer is placed in the drilled hole. This is used as a post and the sutures which are on the tibial side within the bone plug of the ACL graft are then wrapped around the post while pulling traction and keeping the knee flexed approximately 30 degrees and putting posterior pressure on the tibia as these sutures are secured. The screw is tightened against the tibia to secure the graft. The incision area is then thoroughly irrigated with saline.

Sixth, skin and subcutaneous tissue retraction is then accomplished about the patella, thereby exposing the trough or pie-shaped area where the top portion of the autogenous bone-tendon-bone graft had been harvested in the early parts of the procedure. The present invention is then retrieved and the bone reamings earlier collected are used. In the typical case there are approximately 2–3 ml of bone reamings. These reamings are then used as grafting material for the previously created patellar defect. The interior surface of the chamber has a smooth and concave surface to facilitate effective retrieval and scooping out of the reamings. The reamings are scooped out of the collection device 12 by the surgeon using an operating room instrument such as the back end of an Adson's forceps and transferring the graft to the patellar defect. The surgeon compresses the reamings to conform to the defect in the patella. Usually all of the reamings are packed into the defect.

The peritenon which had been previously opened is then brought back over the defect. The peritenon is closed over the defect and the patella, which is now filled with graft material. Closure is continued distally over the patellar tendon. This ensures that the graft material will stay within the defect. The wounds are again irrigated. Two drains are then placed in two separate areas, one in the intraarticular area through the superolateral portal and one in the subcutaneous area where the ACL graft had been harvested. All cannulas are removed and the subcutaneous tissue is closed. The skin is closed. The wounds are sterilely dressed and a knee ranger brace is placed in full extension on the knee. Drains are utilized for 12–24 hours to drain fluid and blood that accumulate in the subcutaneous area and the knee joint. The tourniquet is deflated and the patient is then returned to recovery room.

Another embodiment of the collection device generally indicated at 50 is illustrated in FIGS. 6–9. The collection device 50 includes a collection chamber 52 and a scoop wall 64 and is similar to the collection device 10 illustrated in FIGS. 1–5. The collection device 50, however, as explained in more detail below has a scoop wall 64 that can be bent further and has a wicking mechanism 80 to wick fluid from the bone reamings.

The collection chamber 52 includes a front face 54 and a back face 56 defining an opening 57. As in the collection device 10, the connection between the front face 54 and the back face 56 is seamless and forms an encompassing wall that defines the collection chamber 52. The front face 54 also has a cutout 62 that facilitates the surgeon's use of a reamer. The cutout 62 is the same or very similar to the cutout 22 as illustrated in FIGS. 1–5 including its position, size and orientation. The back face. 56 extends upwardly and includes the scoop wall 64. Similar to the scoop wall 24 of FIGS. 1–5, the scoop wall 64 includes a depression 65 disposed centrally at a top edge 66. The scoop wall 64 along with the collection chamber 52 are formed as an integral unit.

Figure 7:
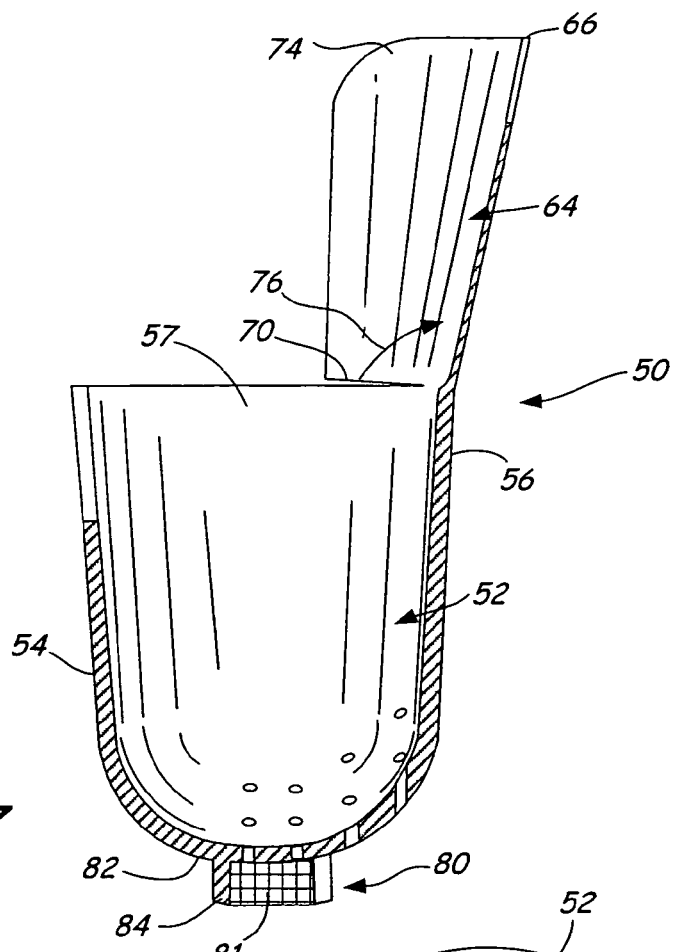
FIG. 7 is a sectional view taken along the line 7—7 in FIG. 6.
Figure 9:
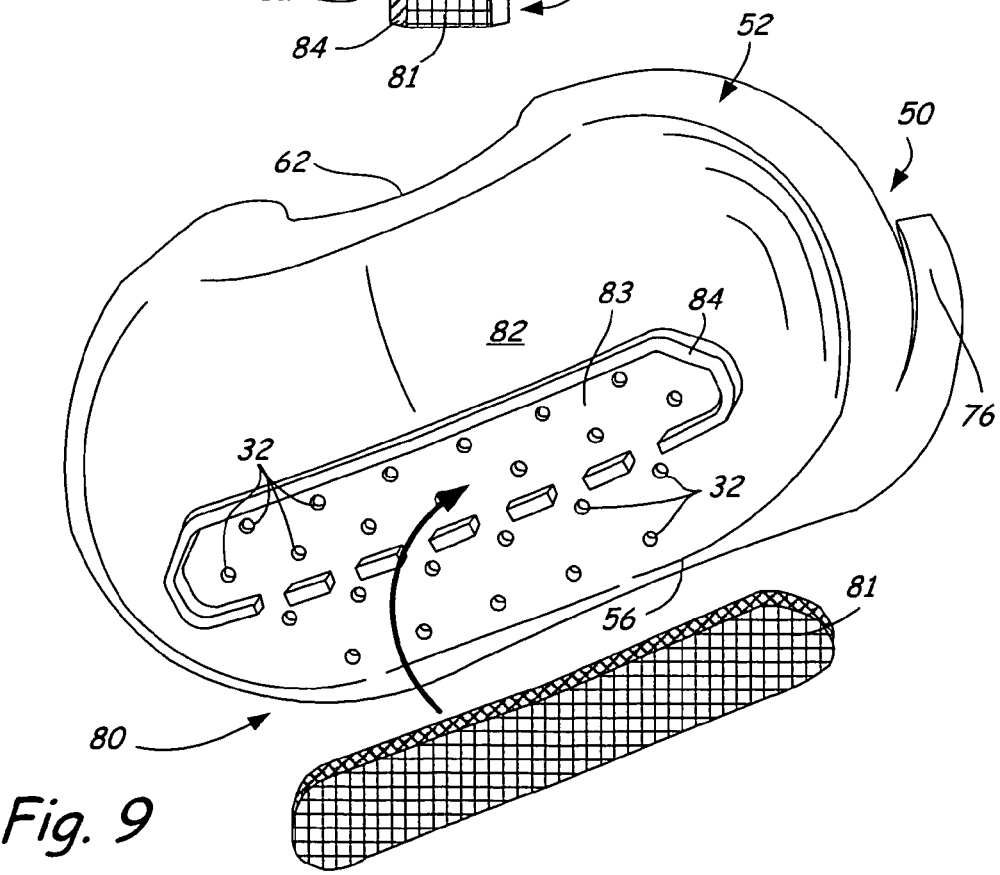
FIG. 9 is a perspective view of the alternative embodiment illustrating the wicking material.
Figure 8:
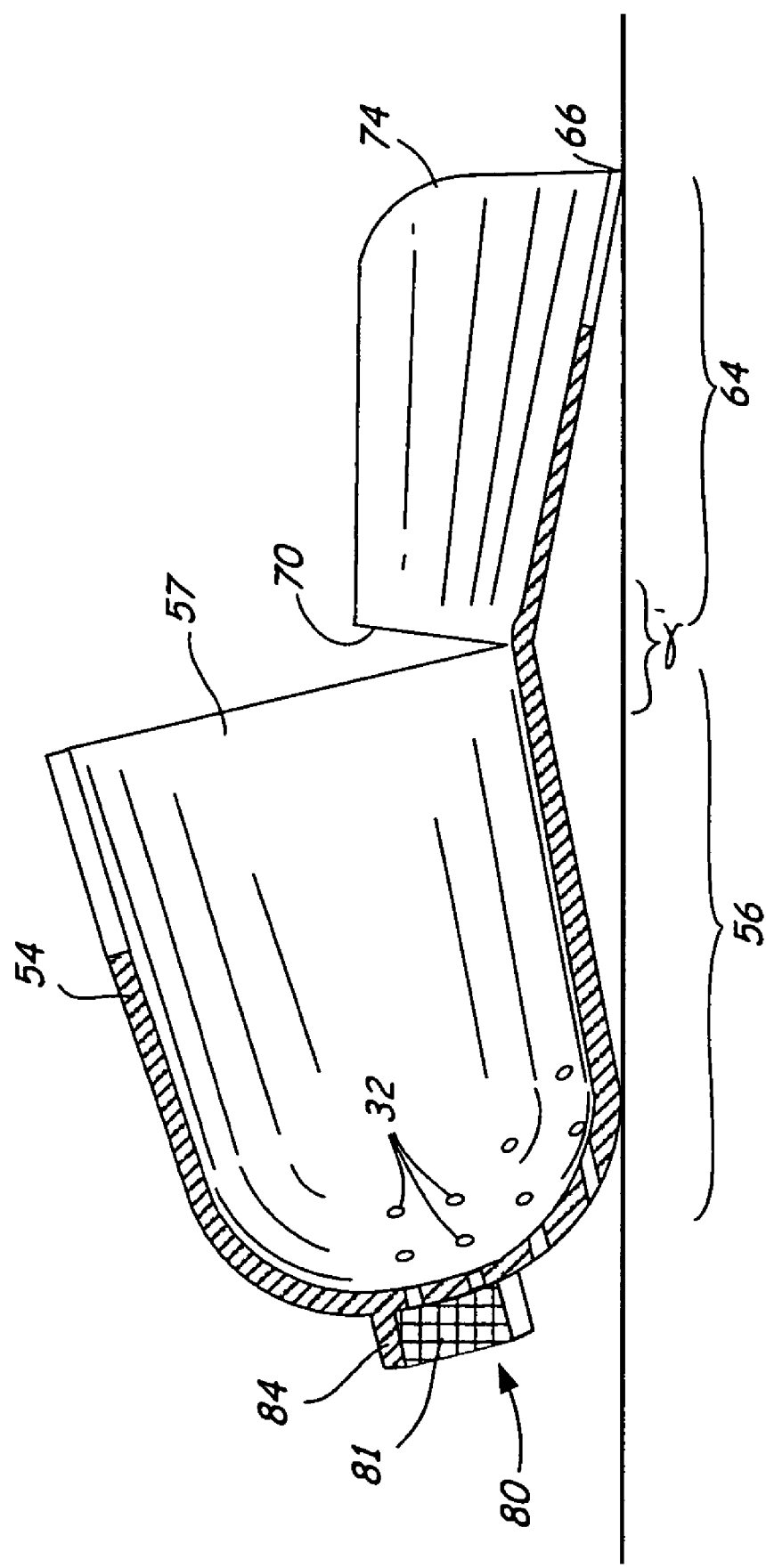
FIG. 8 is a sectional view of the alternative embodiment on a surface in a resting position.

The scoop wall 64 is separated from the chamber 52 along lower edges 70, 72 of left and right wing portions 74 and 76, respectively. The separation between the wing portions 74 and 76 and the collection chamber 52 assist in bending the scoop wall 64 back away from the container portion 52, as indicated by arrow 76 in FIG. 7 and as illustrated in FIG. 8. In addition, a hinging portion 78 between the scoop wall 64 and the container portion 52 is thinned to facilitate bending back the scoop wall 64. One suitable polymer device 50 is polypropylene.

There are at least two reasons for bending the scoop wall 64 considerably more than the embodiment illustrated in FIGS. 1–5. A primary reason for bending the scoop wall 64 back further is to aid the surgeon in retrieving (scooping) the bone reamings out of the collection chamber 52. Moving the scoop wall back further permits better access and a better angle to retrieve bone reamings. Another reason for bending the scoop wall 64 back further is to create a greater angle α' between the collection chamber 52 and the scoop wall 64 when setting the collection device 50 on a flat surface after the reamings are collected, as illustrated in FIG. 8.

Depending on the polymer used to construct the device 50, the wall 64 may also be broken off. Breaking off the wall 64 just prior to retrieving the bone chips provides additional access to the chamber 52.

The collection device 50 also includes a wicking mechanism 80 positioned on a bottom surface 82 of the collection chamber 52. The wicking mechanism 80 includes a protective rail 84 and a wicking material 81. The protective rail 84 extends downwardly from the bottom surface 82 as best illustrated in FIGS. 7 and 8. The wicking material 81 is secured by a suitable adhesive to the bottom surface 82 within an area 83 defined by the rail 84. The wicking material 81 wicks fluid from the bone reamings inside the collection chamber 52 and thereby removing fluid from the bone reamings contained therein to present the bone reamings in a better form for the surgeon to use.

The technique of tibial tunnel reaming, collection and retention, and use of the collected reamings as grafting material to repair the patellar defect is superior to other methods of either not treating the patellar defect or other methods of treating the patellar defect in bone-tendon-bone ACL reconstruction. If the patellar defect is not treated, the patient can feel the defect on their "kneecap" which can have a negative psychological effect. Most patients do not like the feel of that "hole" in their kneecap. The generally accepted practice among orthopedic surgeons is to treat the patellar defect because it is believed that the patella is weaker if not treated.

Using bone reamings is also superior to using a bone core because a bone core is rigid, is more difficult to work with, takes more time for a surgeon, operating room, and staff, for the OR procedure because it has to be sized, cut and formed to fit, is not pliable, and does not fit in the defect as well. Curetting tibial bone from the bottom of the tibia B-T-B graft harvest site also has the same time, difficulty, and resulting cost disadvantages as using a bone core; curetting bone also creates further morbidity to the tibia. It also is illogical to waste the reamings already available with the use of this device and create additional bone "chips" to use in the patella. Other methods using non-autogenous graft material are also more expensive.

The bone reamings provide greater surface area of bone which promotes healing, is more readily accepted by the patient's body, is more pliable for surgeons to use, saves time for the surgeon and OR staff, saves OR costs and time, and is more flexible and molds to the shape of the patellar defect. Prior art methods do not provide these advantages. The method of the present invention also provides use of autogenous grafting material, which optimizes healing and effective recovery for the patient. Use of autogenous material also reduces the risk of infection and disease transmission. This invention makes this technique efficient and effective for the surgeon and operating room staff.

Although the present invention has been described with reference to preferred embodiments, workers skilled in the art will recognize that changes may be made in form and detail without departing from the spirit and scope of the invention.

The invention claimed is:

1. A collection device for collecting material during a surgical procedure, the device comprising:
   a collection chamber defined by an encompassing wall and having an opening sufficient for permitting collection of the material during the surgical procedure;
   a scoop wall extending from the encompassing wall and having a distal end portion for positioning proximate a source of the material and for guiding the material to the collection chamber; and
   a wicking material positioned outside the collection chamber and in fluid association therewith sufficient to wick fluid from within the collection chamber.

2. The collection device of claim 1 and further including at least one aperture for passing fluid from the collection chamber to the wicking material.

3. The collection device of claim 1 wherein the wicking material is positioned along an outside surface of the collection chamber.

4. The collection device of claim 1 wherein the wicking material is framed by a rail extending from the collection chamber and surrounding the wicking material.

5. A collection device for collecting material during a surgical procedure, the device comprising:
   a collection chamber defined by an encompassing wall and having an opening sufficient for permitting collection of the material during the surgical procedure; and
   a scoop wall extending from the encompassing wall and having a distal end portion for positioning proximate a source of the material and for guiding the material to the collection chamber, wherein the scoop wall includes a middle wall portion and sidewall portions extending from opposing sides of the middle wall portion in a generally curved manner to form a channel for guiding the material to the opening and wherein the sidewall portions are separated from the encompassing wall such that the scoop wall is bendable with respect to the chamber.

6. The device of claim 5 wherein the scoop wall is capable of being broken from the collection chamber.

7. The device of claim 5 including a hinged wall section connecting the collection chamber and the scoop wall.

8. The collection device of claim 5 and further comprising:
 a wicking material positioned outside the collection chamber in fluid association therewith sufficient to wick fluid from within the collection chamber.

9. The collection device of claim 8 and further including at least one aperture passing fluid from the collection chamber to the wicking material.

10. The collection device of claim 8 wherein the wicking material is positioned along an outside surface of the collection chamber.

11. The collection device of claim 8 wherein the wicking material is framed by a rail extending from the collection chamber and surrounding the wicking material.

12. A collection device for collecting surgical material during a surgical procedure, the device comprising:
 a collection chamber defined by a wall having a distal portion sufficiently pliant to generally conform to the body proximate to the surgical site from which the surgical material is being collected and positionable proximate a source of the surgical material such that the surgical material is collected within the chamber and a wicking material positioned outside the collection chamber and in fluid association therewith sufficient to wick fluid from within the collection chamber.

13. The collection device of claim 12 and further including at least one aperture for passing fluid from the collection chamber to the wicking material.

14. The collection device of claim 12 wherein the wicking material is positioned along an outside surface of the collection chamber.

15. The collection device of claim 12 wherein the wicking material is framed by a rail extending from the collection chamber and surrounding the wicking material.

16. A collection device for collecting surgical material during a surgical procedure, the device comprising:
 a collection chamber defined by a wall having a distal portion sufficiently pliant to generally conform to the body proximate to the surgical site from which the surgical material is being collected and positionable proximate a source of the surgical material such that the surgical material is collected within the chamber wherein the distal portion of the wall has inwardly extending slot areas approximate an opening of the collection chamber to aid in bending the distal portion.

17. The device of claim 15 and further including a hinging wall section extending from one slot to the other.

18. The collection device of claim 15 and further comprising:
 a wicking material positioned outside the collection chamber in fluid association therewith sufficient to wick fluid from within the collection chamber.

19. The collection device of claim 17 and further including at least one aperture passing fluid from the collection chamber to the wicking material.

20. The collection device of claim 17 wherein the wicking material is positioned along an outside surface of the collection chamber.

21. The collection device of claim 17 wherein the wicking material is framed by a rail extending from the collection chamber and surrounding the wicking material.

* * * * *